United States Patent
Tsuda et al.

(10) Patent No.: US 6,375,808 B1
(45) Date of Patent: Apr. 23, 2002

(54) PROCESS FOR PRODUCING DIFLUOROMETHANE

(75) Inventors: Takehide Tsuda; Takashi Shibanuma; Yasufu Yamada, all of Osaka (JP)

(73) Assignee: Daikin Industries Ltd., Osaka (JP)

(*) Notice: Subject to any disclaimer, the term of this patent is extended or adjusted under 35 U.S.C. 154(b) by 0 days.

(21) Appl. No.: 09/242,699

(22) PCT Filed: Aug. 26, 1997

(86) PCT No.: PCT/JP97/02961

§ 371 Date: Apr. 26, 1999

§ 102(e) Date: Apr. 26, 1999

(87) PCT Pub. No.: WO98/08789

PCT Pub. Date: Mar. 5, 1998

(30) Foreign Application Priority Data

Aug. 27, 1996 (JP) .............................. 8-225290

(51) Int. Cl.$^7$ ................. B01D 3/34; C07C 17/386; C07C 19/08
(52) U.S. Cl. .............. 203/35; 203/77; 203/80; 203/50; 423/240; 423/483; 570/164; 570/178
(58) Field of Search ................ 203/35, 34, 67, 203/42, 91, 77, 80, 73, 50; 570/177, 178, 164; 95/233; 423/240, 483, 488; 510/408

(56) References Cited

U.S. PATENT DOCUMENTS

| | | |
|---|---|---|
| 2,640,086 A | 5/1953 | Baldwin |
| 3,873,629 A | 3/1975 | Jones |
| 3,976,447 A | 8/1976 | Merchant et al. |
| 4,209,470 A | 6/1980 | Lorquet |
| 5,094,773 A | 3/1992 | Manzer et al. |
| 5,523,015 A * | 6/1996 | Tsuda et al. ............ 203/39 |
| 5,707,497 A * | 1/1998 | Galland et al. ......... 203/75 |
| 5,763,708 A * | 6/1998 | Elemmer et al. ........ 570/169 |

FOREIGN PATENT DOCUMENTS

| | | |
|---|---|---|
| EP | 0467531 A1 | 1/1992 |
| GB | 387614 | 2/1933 |
| GB | 1052118 | 12/1966 |
| JP | 5178768 A | 7/1993 |
| JP | 6172228 A | 6/1994 |
| JP | 7258125 A | 10/1995 |
| WO | WO9321140 A1 | 10/1993 |

\* cited by examiner

Primary Examiner—Virginia Manoharan
(74) Attorney, Agent, or Firm—Birch Stewart Kolasch & Birch LLP

(57) ABSTRACT

A process for refining difluoromethane by removing hydrogen fluoride, which is contained in difluoromethane difficult to remove. The process involves distilling a mixture of difluoromethane with hydrogen fluoride where the mixture is in contact with sulfuric acid. The hydrogen fluoride remains in the liquid phase and the difluoromethane goes into the vapor phase.

7 Claims, 1 Drawing Sheet

PROCESS FOR PRODUCING DIFLUOROMETHANE

This application is the national phase under 35 U.S.C. §371 of prior PCT International Application No. PCT/JP97/02961 which has an International filing date of Aug. 26, 1997 which designated the United States of America.

TECHNICAL FIELD

The present invention relates to a process for producing difluoromethane (hereinafter, also referred to as "HFC-32") having a high purity by removing hydrogen fluoride (hereinafter, also referred to as HF) from a mixture of HFC-32 comprising HF, for example a reaction product comprising HFC-32 and HF which product is prepared by a production process for HFC-32 by means of fluorination of dichloromethane (hereinafter, also referred to as "HCC-30").

BACKGROUND ART

Recently, the ozone layer depletion of the stratosphere by means of chlorofluorocarbons has been a serious problem, and the uses thereof are prohibited internationally. Further, productions and uses of hydrochlorofluorocarbons are also restricted. HFC-32 as a compound free from chlorine has an ozone layer destruction factor of zero and thus its global warming factor is small, and has a good freezing capacity, so that HFC-32 is said to be favorable as an alternative cooling medium in place of the chlorofluorocarbons which are restricted.

In order to remove an acidic material, such as HF from the halogenated hydrocarbons, a process would be generally considered, in which the content of such a material is decreased as low as possible through a procedure, for example distillation procedure before washing with water. However, in many case, it is not easy to remove HF from the halogenated hydrocarbons to an extent that the remaining halogenated hydrocarbons may be washed with water since the halogenated hydrocarbons often form a minimum azeotropic mixture with HF.

As a process to remove HF from the azeotropic mixture comprising halogenated hydrocarbons and HF, a process wherein the mixture including HF is chilled to let each component of the mixture separate from each other in liquid phase or layer (so-called liquid phase-liquid phase separation), the upper phase (or layer) mainly comprising HF being recycled to the reaction step, and the lower phase (or layer) mainly comprising halogenated hydrocarbons being distilled to obtain a halogenated hydrocarbons including substantially no HF is disclosed in, for example, U.S. Pat. Nos. 2,640,086; 4,209,470; 5,094,773; EP-A No. 04 67 531 or Japanese Patent Kokai Publication No. 5-178768.

U.S. Pat. No. 3,873,629 discloses a process for continuous separation of HF from chlorodifluoromethane, wherein the gaseous mixture of these two components are counter-currently contacted with sulfuric acid to remove HF.

In addition, U.S. Pat. No. 3,976,447 proposes a process to obtain a halogenated hydrocarbons containing no HF through absorption by particles of calcium chloride, barium chloride or strontium chloride.

Japanese Patent Kokai Publication No. 7-258125 discloses a process for removing HF through two-stage distillation with the azeotropic composition of HFC-32 and HF varying by changing pressure thereof.

The system consisting of HFC-32 and HF does not substantially have a phase-separation point under a commercially operable temperature condition, which is generally above around −30° C., due to mutual dissolution of each components, so that a process using phase separation is not applicable to such a system.

In addition, this system forms a minimum azeotropic mixture. However, since the HF concentration in such an azeotropic composition is too low, a considerable amount of HFC-32 is required to be distilled as an azeotropic mixture with HF in order to remove HF by means of distillation. As to the azeotrope of the system consisting of HFC-32 and HF, International Patent Publication No. WO93/21140 may be referred (the disclosures of this patent Publication is herein incorporated by reference). The distilled HFC-32 is necessary to be recovered from the azeotropic mixture with HF since the amount thereof is considerably large. Therefore, a process to wash the azeotropic mixture with water to remove HF may be considered.

However, the resultant HFC-32 may contain water in an amount up to around the saturation point due to such a water-washing treatment. In order to solve such a problem, use of dehydrating agent comes to be required. Then, use of dehydrating agent for halogenated hydrocarbons yields another problem that the dehydration performance is not so sufficient, and in addition, HFC-32 may be decomposed depending on the kind of the dehydration agent. Further, it is necessary to be considered that HFC-32 is mainly used as a refrigerant, and HFC-32 having a high purity with little water content is desired. When these factors are considered, removing HF from HFC-32 by means of the combination of azeotropic distillation with water washing is not always a preferable process.

The process to vary the azeotropic composition by change of pressure is also not an effective process for the system consisting of HFC-32 and HF since the HF concentration in the azeotropic composition is too low to be required to recycle a large amount of HFC-32 and energy loss due to heating and cooling therethrough is too large.

Thus, the conventional processes for removing HF as described above is neither industrially applicable nor economical.

The above U.S. Patent process in which the mixture of the two components are contacted with sulfuric acid describes that the HF concentration in the chlorodifluoromethane may be decreased from about 3.0% by weight to about 0.2% by weight. However, it is not clear from the disclosure of the aforementioned U.S. Patent whether or not the process may be industrially and effectively applicable to the case addressed by the present invention wherein HFC-32 has less initial HF concentration, for example 0.5% by weight or less since the HF concentrations and the kinds of the fluorohydrocarbons are different from each other.

DISCLOSURE OF INVENTION

Therefore, it is an object of the present invention to provide a process for producing HFC-32 wherein the HF removal from HFC-32 which has been said to be difficult as described above is carried out effectively, and in other words to provide a process for refining HFC-32.

As a result of the inventors' intensive research on the process for refining HFC-32 to effectively remove HF from HFC-32, which has been said to be difficult, the present invention is accomplished.

The present invention is a process to obtain a mixture comprising HFC-32 and reduced content of HF, preferably substantially no HF by means of contacting a mixture comprising HF and HFC-32, for example a mixture having the azeotropic composition thereof (e.g. having a composition wherein the weight by weight ratio of HF/HFC-32 is 1/99 under a temperature of 7.2° C. and at a pressure of 10.2 kg/cm²-abs.) with sulfuric acid, characterized that the HF concentration in the mixture before contact is less than about 1% by weight, preferably less than about 0.5% by weight, the operating pressure at the contact is from 10 to 40 kg/cm²-abs. and the operating temperature is within a range from 10 to 100° C.

Figure 1:
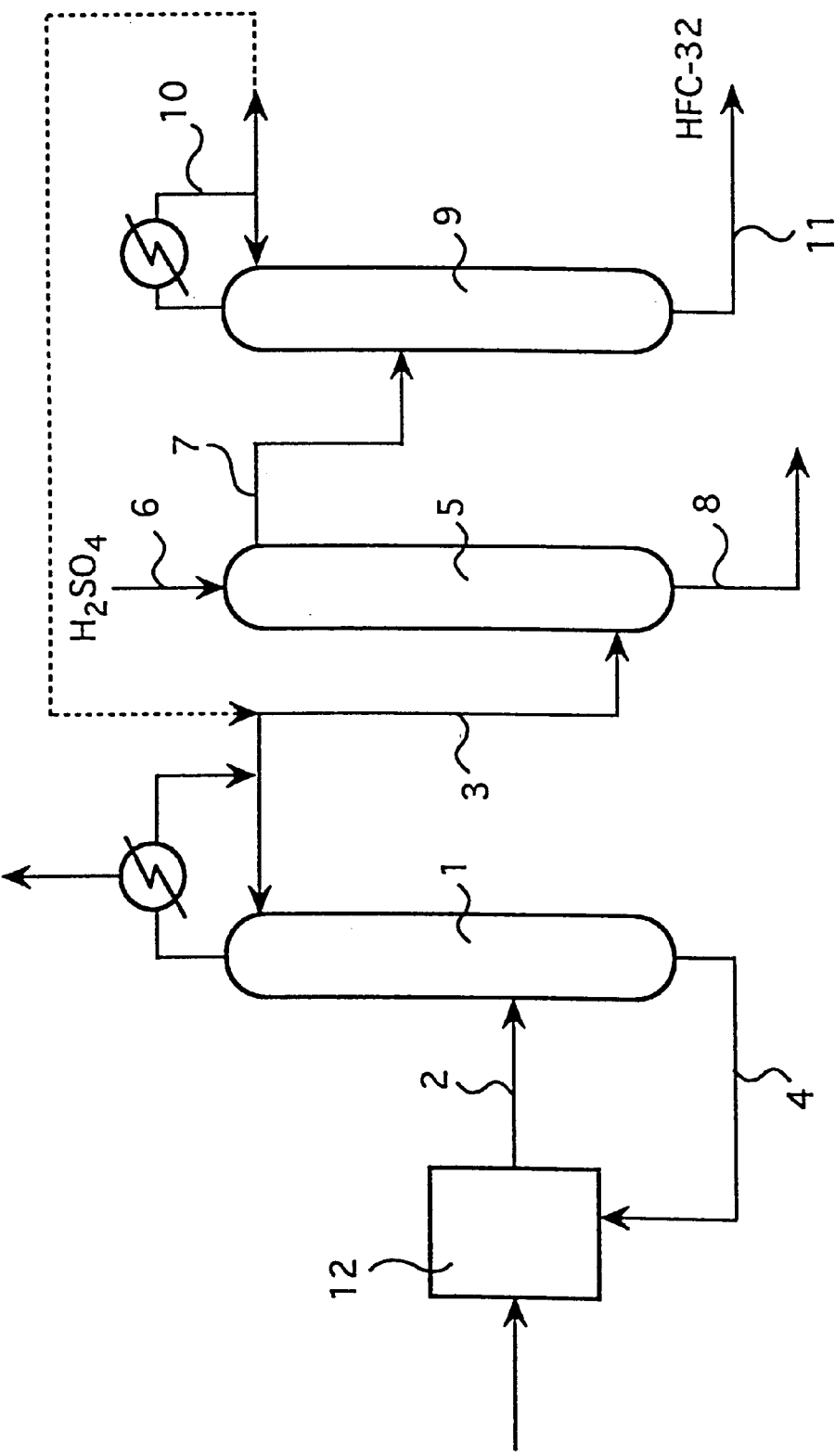
FIG. 1 is a flow sheet schematically showing one preferred example of the process of the present invention.

In the drawing, reference numbers show the followings:
1. first distillation step,
2. feedstock,
3. effluent,
4. bottom product,
5. sulfuric acid contacting tower,
6. sulfuric acid,
7. effluent including HFC-32,
8. bottom product including HF,
9. second distillation step,
10. distillate,
11. bottom product, and
12. reaction step.

DETAILED EXPLANATION OF THE INVENTION

In one embodiment, the present process provides a process for producing HFC-32 wherein the mixture to be contacted with sulfuric acid substantially consists of HFC-32 and HF, and, after the contact, the mixture consists of HFC-32 and a substantially reduced content of HF, preferably the mixture consists of HFC-32 and substantially no HF. Accordingly, HFC-32 the purity of which is increased is obtained by refining through the removal of HF from the above mentioned mixture.

In the present invention, when an expression "hydrogen fluoride content is substantially reduced" is used, it means that the HF content of the mixture after contact is lower than that of before contact (for example, the content is reduced to the value which is almost 10% of the original value, preferably almost 0.1% of the original value), and in general, it equals to the meaning that the HF concentration in the mixture is decreased, for example, to the value which is almost 10% of the original value, preferably almost 0.1% of the original value.

The mixture of the present process, which contacts with sulfuric acid, may be in a liquid phase, in a vapor phase or a mixture thereof, and its condition may be determined depending on the operation pressure, operation temperature and the composition of the mixture.

When the mixture is in a vapor phase, HF mainly transfers from the gaseous mixture to the sulfuric acid phase accompanying a portion of HFC-32 through a general vapor-liquid contact, so that a vapor phase the HF content of which is reduced is obtained and a sulfuric acid phase (liquid phase) the HF content of which is conversely increased is obtained. Thus obtained vapor phase may be subjected to the next step without any treatment or after being liquefied.

When the mixture is in a liquid phase, the mixture is contacted with sulfuric acid by mixing, and then the liquid phase is subjected to a pressure lower than the operation pressure of the contact system and/or a temperature higher than the operation temperature of the contact system. Consequently, the majority of HF is remained in the sulfuric acid phase (liquid phase), while the vapor phase consisting of HFC-32 is generated, which may be recovered and a sulfuric acid phase may be obtained. When the vapor phase is generated, although a small quantity of HF may be included in the vapor phase, the quantity thereof is very small.

When the mixture is a mixture consisting of the liquid phase and the vapor phase, a combination of the above two embodiments may be applied. For example, the liquid phase after the contact, similar to the aforementioned case when the mixture is in the liquid phase, may be subjected to a pressure lower than the operation pressure and/or a temperature higher than the operation temperature of the contact to generate a vapor of HFC-32 which is dissolved in the liquid phase and then the vapor may be recovered. Alternatively, the part that is in a vapor phase from the beginning may be recovered as it is as HFC-32 having a decreased content of HF.

In conjunction with the present invention, there is a process (U.S. Pat. No. 3,873,629) in which a gaseous mixture consisting of HF and chlorodifluoromethane is counter-currently contacted with sulfuric acid as mentioned above. However, the azeotropic composition consisting of, such as HFC-32 and HF addressed by the present invention has a very low HF concentration, which is about 1% by weight or less. Therefore, a decrease of the concentration of HF in the sulfuric acid phase may not be expected under the condition as the above U.S. Patent process, wherein a HF content in sulfuric acid is 5% by weight, the operating temperature is 25° C. and the operating pressure is 3.5 kg/cm²-abs. In fact, when a HFC-32 phase having a HF content of 0.5% by weight was treated at a temperature of 20° C. and a pressure of 1 atm under a condition in which the HF content of the liquid phase-sulfuric acid is 5% by weight, the HF concentration in HFC-32 phase conversely increased to about 0.7% by weight. Accordingly, the inventors carried out an intensive research on the condition for removing HF from a mixture consisting of HFC-32 and HF with sulfuric acid, thereby found that HF may be industrially removed from HFC-32, which resulted in the completion of the present invention.

According to our research on the condition in which the concentration of HF in the HFC-32 phase decreases, we found that when a HF concentration is 0.5% by weight in sulfuric acid phase, the HF concentration in the HFC-32 phase is 475 ppm by weight at an equilibrium state and the HF concentration could no longer be decreased (1 atm, 20° C.). Then, in order to further decrease the HF concentration in the HFC-32 phase, the HF concentrations in the sulfuric acid phases to be used were changed to 0.2% by weight in one case and 0.02% by weight in another case, therethrough the HF concentration in the HFC-32 phase were found to reach equilibrium at about 140 ppm by weight and about 11 ppm by weight (at 1 atm and 20° C.), respectively. In the latter case, the rate of removal of HF is calculated to be 99.8%. In the context of the present invention, the rate of removal is calculated from the following formula:

(rate of removal)=1−(*HF* concentration of *HFC*-32 phase after contact treatment)/(*HF* concentration of *HFC*-32 phase before contact treatment)

Therefore, in this case, the value of the rate of removal of HF is calculated based on as follows:

((5000−11)/5000=0.998).

Thus, it is found that the HF concentration in the HFC-32 phase may be decreased to a very low concentration value by controlling the HF concentration in the sulfuric acid phase.

Accordingly, the following matters are found:

The equilibrium concentration of HF remaining in the HFC-32 mixture varies depending on the concentration of HF in the sulfuric acid phase (liquid phase) which contacts with the mixture as follows;

When the concentration of HF in the liquid sulfuric acid phase is about 1% by weight or less, preferably about 0.2% by weight or less, more preferably 0.02% by weight or less, the attainable HF concentration in the HFC-32 mixture reaches 475 ppm by weight, 143 ppm by weight, and 11 ppm by weight, respectively;

The above results correspond to the cases in which the accomplished rate of removal is 90% by weight or more, 97% by weight or more, and 99.8% by weight or more, respectively;

Therefore, HF may be effectively removed from the HFC-32 phase.

Further, it is also found that the HF concentration in the HFC-32 phase decreases when the operating pressure increases. That is, the HF concentration in the HFC-32 phase may be further decreased by increasing the pressure of the contacting system. In such a case, the HF concentration may decreases inversely proportional to the operating pressure. For example, when the HF concentration in sulfuric acid is limited to 0.02% by weight or less under a condition that the system has an operating pressure of 10 $kg/cm^2$-abs., a HF concentration in HFC-32 phase of about 1 ppm by weight or less may be attained. When the industrial operation is considered, the operating pressure is preferably in the range from 10 to 40 $kg/cm^2$-abs., more preferably in the range from 20 to 30 $kg/cm^2$-abs.

According to the present process, the temperature at the contact step may influence the HF concentration in the HFC-32 phase that is in equilibrium with the HF concentration in the sulfuric acid phase, however its extent is relatively small. Therefore, the temperature of the contact step may not be particularly limited when it is within a range that is industrially attainable, and the contact step may generally be operated in a temperature range from 10 to 100° C., preferably from 10 to 70° C., and more preferably from 10 to 50° C.

In the present process, the contact of the mixture with sulfuric acid may be carried out using any suitable vapor-liquid contacting apparatus or liquid-liquid contacting apparatus. For example, multi-stage column, packed column or agitating vessel may be used. When the mixture is in a vapor phase, the contacting procedure may be carried out in any procedure, for example selected from co-current flow, cross current flow and counter-current flow procedure. In general, it may be mostly preferred to operate in a counter-current flow procedure.

In the present process, the amounts of the mixture and sulfuric acid to be contacted with the mixture are not particularly limited, and the amounts of sulfuric acid and the HF concentration in the sulfuric acid to be contacted with the sulfuric acid may be determined so that the HF concentration in the HFC-32 phase to be aimed is attained. In principle, the more the amount of sulfuric acid to be used increases, the more the amount of HF which may be removed from the mixture comprising HFC-32 increases. However much the amount of sulfuric acid to be contacted would be increased, a HF concentration in the HFC-32 phase that is smaller than the concentration thereof in the HFC-32 phase which is in equilibrium with the HF concentration in the sulfuric acid phase mentioned above may not be attained, unless the temperature and/or pressure condition would be changed. In general, the ratio of the amount of the mixture to that of the sulfuric acid to be contacted with the mixture may be from about 0.2 to about 4, preferably from about 0.3 to about 1, based on the weight to be introduced into the contacting step.

The present process may be applied to industrial and efficient removal of HF from an HFC-32 phase. It is effective in the case when a HF-32 phase including substantially no HF is aimed to obtain by means of removing unreacted HF from the mixture vapor phase that is generated by the HFC-32 production step.

In such a case, the present process may be applied to the separation of HF not only from the mixture consisting of HF and HFC-32, but also from the product obtained from the production of HFC-32 by fluorination of dichloromethane with HF, which may contain various reaction by-products in addition to HF, HFC-32 and dichloromethane. The production of HFC-32 may be carried out through the known procedures, for example, through liquid phase procedure using antimony chlorofluoride as a catalyst or vapor phase procedure using chromium oxidefluoride as a catalyst. Accordingly, the mixture to which the present process is applicable may include, in addition to HF and HF-32, hydrogen chloride, dichloromethane, chlorofluoromethane, trifluoromethane and/or chlorine existing at various ratio. According to the present process, even in the case when the mixture includes various compounds in addition to HF and HFC-32, the HF content of the mixture substantially decreases and, as to the other compounds, the concentration thereof may vary depending to the affinity thereof for sulfuric acid.

As mentioned above, since HFC-32 forms a minimum azeotropic mixture with HF, removal of HF from halogenated hydrocarbons by merely a distillation procedure is not effective, or is practically difficult. Therefore, the removal of HF from halogenated hydrocarbons may be effectively carried out by shifting the HF content of the azeotropic composition to the other state wherein the HF content is smaller than that of the azeotropic composition by means of any other procedure, for example, phase-separation, such as liquid-liquid phase separation, absorption or pressure change.

That is, when the mixture substantially consists of HF and HFC-32, a mixture of HF and HFC-32 having less HF concentration relative to that of the azeotropic composition is subjected to contacting with sulfuric acid based on the present process; and the obtainable mixture is then distilled to remove substantially the whole HF from the towerhead as an azeotropic mixture with HFC-32. The total amount of the azeotropic mixture is considerably decreased since the HF content is already decreased, so that it may be recycled to the contacting step with sulfuric acid or disposed as it is because its amount is small; while HFC-32 including substantially no HF may be recovered from the towerbottom. Further, when the HF concentration in the HFC-32 phase could be decreased to the permissible concentration, for example about 1 ppm or less, the obtainable HFC-32 phase may be fed as a final product by omitting the distillation procedure which is the following procedure.

When the mixture includes the other components in addition to HF and HFC-32, such other components behave depending on the properties thereof, for example in any embodiments of behaving together with HF, together with HFC-32 and together with both HF and HFC-32. Therefore, as to the behavior of HF and HFC-32, it does not substantially differ from the case when the other components do not exist.

Concrete Embodiments to Carry Out the Invention

Next, the present invention will be explained concretely with reference to the accompanied drawing. FIG. 1 schematically shows one preferable embodiment of the present invention by means of a flow sheet.

In FIG. 1, the feed mixture 2 comprising HF and HFC-32 (generally including an excess amount of HF relative to the azeotropic composition of HF and HFC-32) obtained from the process 12 for the production of HFC-32 is continuously supplied to a first distillation column 1. Operating the distillation operation by means of the above condition, a compound having a boiling temperature lower than those of hydrogen chloride and HFC-32, for example, trifluoromethane is withdrawn and HF and HFC-32 may be distilled off from the top of the column as a distillate 3. A mixture which contains the remained compounds having a boiling temperature higher than those of HF and HFC-32, for example chlorofluoromethane and/or dichloromethane is withdrawn from the towerbottom as a bottom product 4. Since the distillate 3 is an azeotropic composition, HF may not be concentrated any further in the course of the first distillation step. Then, thus obtained distillate 3 is supplied as a mixture to the bottom of the sulfuric acid contacting tower 5 wherein the present process is carried out, and is counter-currently contacted with sulfuric acid 6 which is supplied from the towerhead in a vapor-liquid contact. By such a procedure, while the distillate 3 ascends through the tower in a vapor phase, HF which exists in the distillate 3 is absorbed by sulfuric acid (accordingly, the composition of the distillate 3 shifts toward another composition the HF content of which is less than that of the azeotropic composition), so that a HFC-32 phase including less amount of HF than that of the feedstock is discharged as an effluent 7 from the towerhead. From the towerbottom, a mixture comprising sulfuric acid which absorbed HF when it descends through the tower, and HFC-32 which is dissolved into sulfuric acid is obtained as a bottom product 8.

The effluent 7 is supplied to a second distillation tower 9 and subjected to another distillation procedure, so that an azeotropic mixture consisting of HF and HFC-32 is distilled from the towerhead as a distillate 10 and a HFC-32 phase which includes substantially no HF is obtained as a bottom product 11. This distillate may be recycled to the sulfuric acid contacting tower 5 (via line shown by the dotted line) so that a loss of HF is avoided.

When the effluent 7 from the sulfuric acid contacting tower includes substantially no HF, the distillate 10 from the second distillation tower does not include the azeotropic mixture of HF and HFC-32. In addition, when the distillate 3 from the first distillation tower substantially does not include any compound other than HF and HFC-32 and the effluent 7 includes substantially no HF (for example, its HF content is less than the permissible concentration for HF in the HFC-32 phase, such as about 1 ppm or less), the second distillation tower may be omitted and the effluent 7 may be used as the final product.

The bottom product 4 generally includes a large amount of HF, so that it is preferably recycled to the reaction step. The bottom product 8 also includes HFC-32 component. Accordingly, the bottom product 8 is preferably subjected to a pressure condition which is lower than the operation pressure and/or a temperature condition which is higher than the operation temperature of the contact system, thereby the HFC-32 component dissolved in the bottom product 8 is vaporized and recovered. Since thus recovered vapor phase also includes a small amount of HF that may be simultaneously vaporized, it may be recycled to the first distillation tower 1. The sulfuric acid phase from which the vapor phase was recycled may be recycled to the sulfuric acid contacting tower 5 when the HF concentration thereof is within the permissible range, or may be utilized for the other applications.

INDUSTRIAL APPLICABILITY

According to the present process for the production of difluoromethane, the mixture of difluoromethane including HF is subjected to contact with sulfuric acid so that HF, which has been considered to be difficult to be removed, is easily removed from difluoromethane, whereby difluoromethane can be obtained at its higher concentration.

EXAMPLES

Next, the present invention will be explained in detail with reference to Examples.

Example 1

Into a pressure resistant vessel made of fluoroplastics, in which sulfuric acid having a concentration of 98% by weight was already introduced, an azeotropic mixture of HF and HFC-32 (0.5/99.5% by weight) was continuously supplied in a vapor phase (under atmospheric pressure and at a temperature of 20° C.). It is suitably sampled and determined the HF concentrations of the liquid phase (sulfuric acid phase) and the vapor phase (HFC-32 phase) of each sample.

The results are shown in Table 1.

TABLE 1

| HF conc. in Liq-P (*1) (% by weight) | HF conc. in Vap-P (*2) (ppm by weight) | rate of removal-HF (*3) (%) |
|---|---|---|
| 0.02 | 10.7 | 99.8 |
| 0.2 | 142.8 | 97.1 |
| 1 | 475.3 | 90.5 |
| 2 | 3571.5 | 28.5 |

(*1): HF concentration in liquid phase
(*2): HF concentration in vapor phase
(*3): rate of removal of HF According to the results of Table 1, the rate of removal of HF from the azeotropic mixture comprising HF and HFC-32 is found to vary depending on the HF concentration of sulfuric acid in the liquid phase sulfuric acid. In order to accomplish a rate of removal at about 90% by weight or more, the operation must be carried out, keeping the HF concentration in the liquid phase sulfuric acid, which contacts with the mixture, at about 1% by weight or less.

Example 2

Using an apparatus almost the same as the Example 1 and changing operation pressures to 10 kg/cm$^2$ G and 20 kg/cm$^2$ G, the HF concentration in the vapor phase was determined when the HF concentration of the liquid sulfuric acid phase was 1% by weight at 20° C. As a result, the HF concentration in the vapor phase was decreased to one-tenth and one-twentieth of the case using an atmospheric pressure, respectively. According to this example, it is found that HF concentration decreases inversely proportional to the operating pressure.

Example 3

Using an absorbing tower having a diameter of 150 mm and 10 theoretical plates, a HFC-32 mixture (in a vapor phase) including about 5000 ppm by weight of HF was supplied at a rate of 4.8 Nm$^3$/hour and counter-currently contacted with sulfuric acid supplied at a rate of 12 kg/hour at a temperature of 40° C. and a pressure of 20 kg/cm$^2$ G. As a result of this procedure, the HF concentration in the sulfuric acid phase (flow rate: 12 kg/hour) discharged from the towerbottom was 0.5% by weight, while the HF concentration in the gaseous HFC-32 phase (flow rate: 4.8 Nm$^3$/hour) flowing out of towerhead was 10 ppm.

According to the above result, it is found that HF may be easily and continuously removed through an absorption procedure in which HFC-32 including HF is absorbed by (contacted with) sulfuric acid.

What is claimed is:

1. A process for reducing hydrogen fluoride content in a mixture of difluoromethane and hydrogen fluoride, which comprises contacting a first mixture comprising difluoromethane and hydrogen fluoride having a hydrogen fluoride content of not larger than 1% by weight with sulfuric acid at a pressure in the range from 10 to 40 kg/cm$^2$ and a temperature in the range from 10 to 100° C. so as to transfer hydrogen fluoride in the first mixture to sulfuric acid, and thereby obtain a second mixture comprising difluoromethane, wherein at least 90 percent of hydrogen fluoride is removed into sulfuric acid.

2. The process according to claim 1, wherein each of the first and second mixtures consists essentially of difluoromethane and hydrogen fluoride.

3. The process according to claim 1, wherein the first mixture is an azeotropic mixture of difluoromethane and hydrogen fluoride.

4. The process according to claim 1, wherein the first mixture is a product formed by fluorination of dichloromethane with hydrogen fluoride.

5. The process according to claim 1, wherein a hydrogen fluoride content of sulfuric acids which is to contact with the first mixture is not larger than 1% by weight.

6. The process according to claim 1 further comprising a step wherein sulfuric acid, which has contacted with the first mixture is subjected to a lower pressure so that difluoromethane which has been transferred to sulfuric acid is recovered.

7. The process according to claim 1 further comprising a step wherein the second mixture is thereafter subjected to distillation.

* * * * *